United States Patent [19]

Borden

[11] Patent Number: 5,247,188
[45] Date of Patent: Sep. 21, 1993

[54] CONCENTRATOR FUNNEL FOR VACUUM LINE PARTICLE MONITORS

[75] Inventor: Peter G. Borden, San Mateo, Calif.

[73] Assignee: High Yield Technology, Sunnyvale, Calif.

[21] Appl. No.: 824,663

[22] Filed: Jan. 23, 1992

[51] Int. Cl.⁵ ..................... G01N 15/06; G01N 21/00
[52] U.S. Cl. ..................... 250/574; 356/338
[58] Field of Search ............... 250/573, 574, 575, 576; 356/338, 337, 342, 244, 246

[56] References Cited

U.S. PATENT DOCUMENTS

| | | | |
|---|---|---|---|
| 2,812,686 | 11/1957 | Sinclair | 356/338 |
| 4,547,075 | 10/1985 | Fei | 356/72 |
| 4,874,243 | 10/1989 | Perren | 356/342 |
| 4,979,822 | 12/1990 | Sommer | 356/338 |
| 5,087,823 | 2/1992 | Silvy et al. | 356/338 |
| 5,092,675 | 3/1992 | Sommer | 356/338 |
| 5,125,737 | 6/1992 | Rodriguez et al. | 356/338 |

FOREIGN PATENT DOCUMENTS 0144548  7/1986  Japan ..................... 356/337

Primary Examiner—David C. Nelms
Assistant Examiner—Michael Messinger
Attorney, Agent, or Firm—Skjerven, Morrill, MacPherson, Franklin & Friel

[57] ABSTRACT

A converging funnel is placed in an exhaust line to direct substantially all the gas flow in the exhaust line to the sensing laser beam of a particle sensor, thereby preventing deposition of species carried by the gas from depositing on the particle sensor. By concentrating substantially all gas flow through the laser beam, the particle count rate is increased because substantially all particles carried by the exhaust gas is channeled through the laser beam. Further, the particle sensor is also prevented from adverse heating effects of the exhaust gas. In one embodiment, the converging funnel is mounted to the interior wall of the exhaust line by a centering ring.

10 Claims, 2 Drawing Sheets

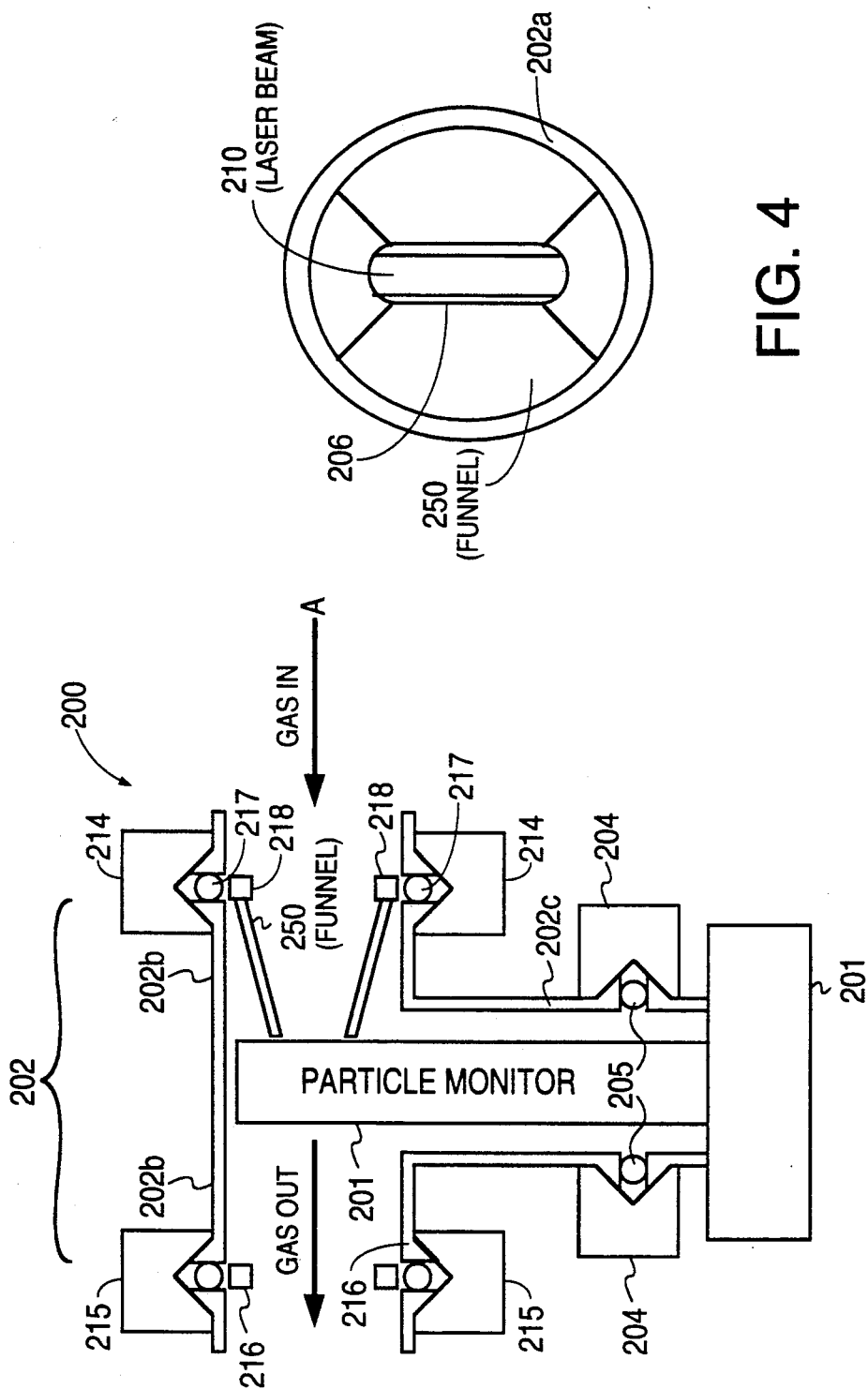

CONCENTRATOR FUNNEL FOR VACUUM LINE PARTICLE MONITORS

FIELD OF THE INVENTION

This invention relates to particle monitors, and in particular, to particle monitors used in the exhaust lines of vacuum process equipment.

BACKGROUND OF THE INVENTION

Particle monitors or sensors are commonly used in vacuum lines, such as exhaust lines of vacuum processing equipment for manufacturing semiconductor integrated circuits. Because many processes are run at intermediate pressures (e.g. between 0.1 to 5 Torr), the gas in an exhaust line in any such process is sufficiently dense to resist free fall of particles. Consequently, particles from the process reactor may be carried by the gas flow in the exhaust line, so that a particle sensor mounted in the exhaust line can be used to monitor such particles. An example of such particle sensor is described in copending application, Ser. No. 07/582,718, entitled "High Sensitivity, Large Detection Area Particle Sensor for Vacuum Applications," by Peter Borden et al., hereby incorporated by reference in its entirety. The particle sensor described in the above copending Application uses a laser beam to measure the rate of particles passing through a cross section of the laser beam.

FIG. 1 is a side sectional view of a vacuum line 100, in which a particle sensor 101 is mounted in a tee section 102 of a vacuum line. As shown in FIG. 1, tee section 102 is placed in line with the exhaust flow, which enters tee section 102 in a direction A at leg 102a and exits tee section 102 at leg 102b. Particle sensor 101 is plugged into the third leg 102c of tee section 102. Each vacuum connection in vacuum line 100 is made using the combination of an O-ring and a clamp ring, such as O-ring 103 and clamp ring 104. O-ring 103 is held in place by a centering ring (not shown), which is a metal ring hugging the inner circumference of the O-ring 103. Flanges, such as flange 105 in leg 102c, are provided so that the O-ring and the clamp ring can form a tight seal at the vacuum connection point.

FIG. 2 is a view of tee section 102 looking into the gas inlet (i.e. leg 102a) in direction A of gas flow. As shown in FIG. 2, particle sensor 101 has an opening 106 exposing a portion of sensing laser beam 110 projecting in a substantially parallel manner to opening 106, and orthogonal to the direction of gas flow. A portion of the exhaust gas, including the particles carried therein passes through opening 106 and sensing laser beam 110. Sensing laser beam 110 counts the particles in the portion of exhaust gas passing through it. As can be readily seen in FIG. 2, a large surface area of particle sensor 101, including its optics, is bathed in the process gas flow.

Alternatively, it is possible to place particle sensor 101 and its optics external to the pipe, and provide in vacuum line 100 windows ("sensor windows") through which sensing laser beam 110 can pass to allow detection of particles in the gas flow. In this configuration, these windows are fully exposed to the effluent gasses in the exhaust line.

Since the particle sensor is placed at a location where the process is not perturbed by the particle monitor's preference, monitoring particles using a particle sensor in the exhaust line, as provided by one of the configurations above, is an attractive technique. However, a particle sensor placed in such location may experience problems from coating, temperature and low count rate.

Specifically, many component gasses of a process effluent are species that will deposit on the exposed surface or surfaces of the particle sensor, or on the sensor windows. For example, in a chemical vapor deposition (CVD) process, the effluent gas flow contains the specie (e.g. silicon dioxide or silicon nitride) sought to be deposited on the target in the process chamber. As the effluent passses by the particle sensor in the vacuum line, the specie in the effluent gas will also be deposited on the exposed portions of the particle sensor. In addition, reaction byproducts may also be deposited. For example, in a tungsten process, byproduct tungsten oxy-fluoride compounds carried by the effluent may be deposited on the same exposed surfaces of the particle sensor. Naturally, such depositions may adversely affect sensor performance.

Further, the exhaust gasses in a vacuum line are often at elevated temperatures. For example, a CVD process may operate at 400°–800° C. Thus, although the temperature of the effluent gasses may have been lowered by the time the particle sensor is reached, bathing the particle sensor or the sensor windows in relatively hot gasses over a period of time may affect sensor performance adversely.

Since a particle sensor is often mounted in a vacuum line of fairly large diameter (e.g. 1.5 to 2 inches), the flow of gas and particles is fairly evenly distributed over the cross section area of the vacuum line. Consequently, in a particle counter, such as the laser beam-based particle counter mentioned above, a relatively low fraction of the particles actually go through the sensing laser beam, resulting in a low particle count. Particle count accuracy can be enhanced if more particles are channeled through the laser beam.

SUMMARY OF THE INVENTION

In accordance with the present invention, a structure for concentrating gas flow is placed in a vacuum line to direct the gas flow to a sensing laser beam of a particle sensor.

In one embodiment, the structure is in the shape of a funnel having a gas entry point having substantially the same cross sectional area as the cross sectional area of the vacuum line, and a gas exit point having both a cross sectional area and a shape substantially the same as those of a selected portion of the laser beam opposite to the gas exit point of the funnel. In this embodiment, the structure is mounted onto the inside wall of the vacuum line by a centering ring.

The present invention provides that substantially the full particle flow is directed through the sensing laser beam, thereby increasing the particle count rate. At the same time, the gas flow is directed away from the exposed surfaces of the particle sensor, thereby preventing contact with the particle sensor and its optics. As a result, the effluent's coating and heating effects on the particle sensor are minimized. Thus, the present invention enhances sensor longevity and performance.

BRIEF DESCRIPTION OF THE DRAWINGS

FIG. 3 is a side sectional view of a vacuum line 200, in which a funnel 250 of the present invention is placed in a the section 202 to direct gas flow in the vacuum line through the sensing laser beam 210 of particle sensor 201, in accordance with the present invention.

FIG. 4 is a sectional view looking into the gas inlet 202a of FIG. 3's tee section 202 in the direction A of gas flow.

DETAILED DESCRIPTION OF THE PREFERRED EMBODIMENTS

Figure 2:
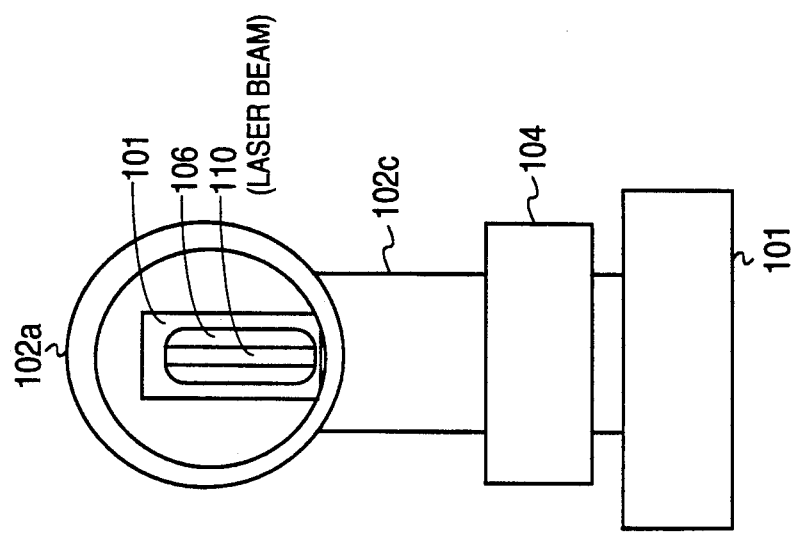
FIG. 2 is a sectional view looking into the gas inlet 102a of FIG. 1's tee section 102 in the direction A of gas flow.
Figure 1:
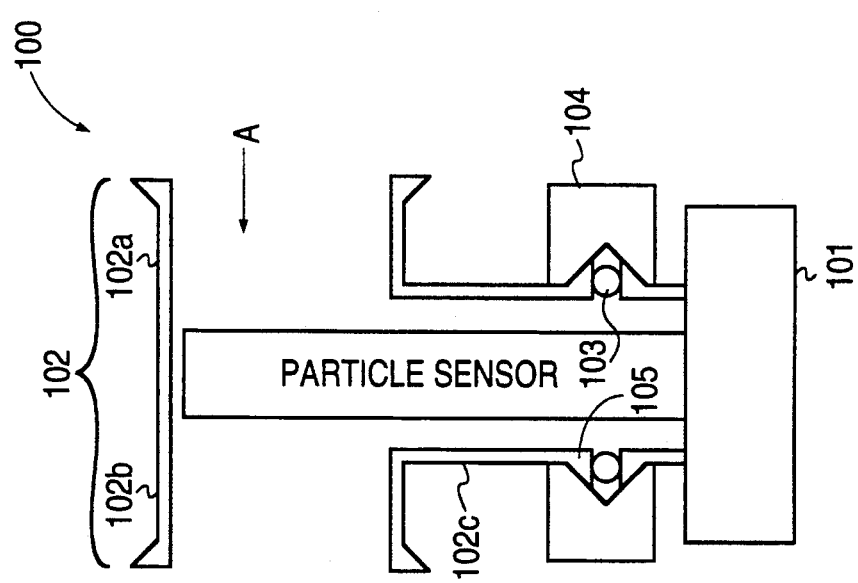
FIG. 1 is a side sectional view of a vacuum line 100, in which a particle sensor 101 is placed inside a tee section 102 of the vacuum line.

FIG. 3 is a side sectional view of an embodiment of the present invention. As shown in FIG. 3, a sensor 201 is mounted in a vacuum line 200 to a leg 202c of a tee section 202, using clamp 204 and O-ring 205. A concentrating funnel 250 is placed in the vacuum line 200 to concentrate the gas flow in vacuum line 200 to a small area defined by the opening 206 at the tapered end of funnel 250. The tapered end of funnel 250 is positioned opposite a sensing portion of the sensing laser beam 210. Funnel 250 is placed on the upstream side of the particle sensor 206 and affixed to the centering ring 218 on which the O-ring 217 mounts. Opening 206 matches the size and shape of a sensing area in sensing laser beam 210. Opening 206 is placed a small distance, e.g. 2 to 5 mm, away from laser beam 210, to avoid interfering with the operation of laser beam 210.

FIG. 4 is a sectional view in vacuum line 200 looking into leg 202a of tee section 202. FIG. 4 shows opening 206 of funnel 250 directly opposite a portion of sensing laser beam 210, and having a shape approximating a portion of the detection area covered by sensing laser beam 210.

One advantage of funnel 250 concentrates the gas flow through sensing laser beam 210. Funnel 250 can be stamped out of aluminum. Funnel 250 can also be formed out of several flat sections of stainless steel, which are bent and spot welded together.

The effects of funnel 250 on the gas flow through the vacuum line 200 include an increase in the gas velocity at the sensing laser beam 210, and a decrease in the total conductance of vacuum line 200 as a result of the constriction at opening 206. The velocity increases by approximately the ratio between the cross sectional area of vacuum line 200 and the cross sectional area of opening 206. For example, if vacuum line has a diameter of 1.5" and the funnel opening has dimensions 0.25" × 1.0", then the velocity of gas at the sensing laser beam 210 increases by a factor of 7.1. Thus, if the velocity is originally 0.5 meter/sec without funnel 250, then the velocity of gas emerging from funnel 250 is about 3.5 meters/sec. Particle sensor 201 should account for this higher gas velocity by having an increased detection bandwidth.

As mentioned above, the total conductance of the vacuum line 200 decreases due to the presence of funnel 250. The conductance of a circular cross-section vacuum line is given by the formula (See Roth, "Vacuum Technology," North Holland (Amsterdam), 1982, page 76):

$$C = 182 \frac{D^4}{L} P.$$

where
C is the conductance in liters/sec,
D is the diameter in cm,
L is the length in cm, and
P is the average of the pressures at the two ends on the line in Torr.

Compared to the circular aperture of vacuum line 200, the conductance of a substantially rectangular aperture, such as opening 206, is more difficult to calculate. Nevertheless, such conductance should be at least the conductance of a rectangular pipe of the cross sectional dimensions of the rectangular aperture. The conductance of a rectangular pipe is given by:

$$C = 260 \; YA^2 \frac{P}{L},$$

where A is the cross-section area in square cm, and Y the quantity is given by the expression:

$$Y = .032333 + 2.1732 \frac{a}{b} - 1.2197 \left(\frac{a}{b}\right)^2,$$

in which a and b are the lengths of the two sides of the aperture.

The presence of funnel 250 reduces the total conductance of vacuum line 200 by a factor which is estimated to be no more than the ratio of the conductances computed above for pipes of circular and rectangular cross-sections; this ratio is given by:

$$\text{Ratio} = 1.4Y \left(\frac{A}{D^2}\right)^2$$

Hence, for the aperture parameters given above (i.e. A=0.25 square inches, D=1.5 inches, Y=0.5), the conductance changes by a factor of 0.0086. For example, the conductance of a vacuum line 2 meters long and 4 cm in diameter is about 200 liters/sec at 1 Torr, so that the conductance of opening 206 at 1 Torr is at least 1.7 liters/sec. For many applications in semiconductor processing, such conductance is sufficient, since the conductance of the line is normally throttled to control the pressure in the process chamber. Considering that opening 206 is short in the direction of gas flow, the actual conductance is considerably higher than the estimate provided above.

The above detailed description is provided to illustrate the specific embodiments of the present invention and not intended to be limiting. Numerous modifications and variations within the scope of the present invention are possible. For example, particle sensor 201 can be placed external to vacuum line 200. In such configuration, laser beam 210 is admitted through a first window, with the detector portion of particle sensor 201 located to measure the light scattering through another window opposite the first window in sensing laser beam 210's direction of propagation. Another variation provides that opening 206 be built integral to vacuum line 200, rather than mounted by a centering ring. Concentration funnel 250 can have an entry opening, or have walls of arbitrarily steep angle, so that the gas entry opening has a cross-section area substantially equal to that of the gas exit opening. The present invention is defined by the following claims.

We claim:

1. A method for concentrating gas flow in a vacuum line to allow particle monitoring by a laser beam of a particle sensor, said laser beam having a portion exposed to said vacuum line, said method comprising the steps of:

providing a structure having entry and exit openings, said structure being enclosed other than at said entry and exit openings, wherein said exit opening approximates the shape and size of said exposed portion of said laser beam; and mounting said structure in said vacuum line such that said exit opening is immediately in front of said exposed portion of said laser beam so as to concentrate said gas flow through said laser beam, thereby preventing said gas flow from contacting said particle sensor.

2. A method as in claim 1, wherein said step of providing a structure provides said entry opening a cross section substantially the cross section of said vacuum line.

3. A method as in claim 1, wherein said mounting step mounts said structure onto the inside of said vacuum line using a centering ring.

4. A method as in claim 1, wherein said step of providing a structure provides said structure in the shape of a funnel.

5. A method as in claim 1, wherein said mounting step mounts said structure in a first leg of a tee section, and wherein said particle sensor is mounted in a second leg of said tee section.

6. An apparatus for concentrating gas flow in a vacuum line to allow particle monitoring by a laser beam of a particle sensor, said laser beam having a portion exposed to said vacuum line, said apparatus comprising:

a structure having entry and exit openings, said structure being enclosed other than at said entry and exit openings, wherein said exit opening approximates the shape and size of said exposed portion of said laser beam; and means for mounting said structure in said vacuum line such that said exit opening is immediately in front of said exposed portion of said laser beam so as to concentrate said gas flow through said laser beam, thereby preventing said gas flow from contacting said particle sensor.

7. An apparatus as in claim 6, wherein said entry opening of said structure has a cross section substantially the cross section of said vacuum line.

8. An apparatus as in claim 6, wherein said means for a structure comprises a centering ring for mounting said structure onto the inside of said vacuum line.

9. An apparatus as in claim 6, wherein said structure has the shape of a funnel.

10. An apparatus as in claim 6, wherein said means for mounting a structure mounts said structure in a first leg of a tee section, and wherein said particle sensor is mounted in a second leg of said tee section.

* * * * *